United States Patent [19]

Noddin et al.

[11] Patent Number: 4,906,241
[45] Date of Patent: Mar. 6, 1990

[54] DILATION BALLOON

[75] Inventors: Richard A. Noddin, Holliston; Arthur R. Madenjian, Waltham; Ralph J. Barry, Jr., Hudson; Fernando A. de Toledo, Concord; Richard M. DeMello, Acton, all of Mass.

[73] Assignee: Boston Scientific Corporation, Watertown, Mass.

[21] Appl. No.: 170,164

[22] Filed: Mar. 18, 1988

Related U.S. Application Data

[63] Continuation-in-part of Ser. No. 126,769, Nov. 30, 1987.

[51] Int. Cl.[4] .............................................. A61M 29/02
[52] U.S. Cl. ....................................... 606/194; 604/96
[58] Field of Search ............ 128/344, 325, 343, 348.1; 604/96–103

[56] References Cited

U.S. PATENT DOCUMENTS

| | | |
|---|---|---|
| 3,467,101 | 9/1969 | Fogarty et al. . |
| 3,572,315 | 3/1971 | Cullen, II . |
| 3,854,484 | 12/1974 | Jackson . |
| 3,913,565 | 10/1975 | Kawahara . |
| 4,004,588 | 1/1977 | Alexander . |
| 4,263,917 | 4/1981 | Moss . |
| 4,276,874 | 7/1981 | Wolvek et al. . |
| 4,299,227 | 11/1981 | Lincoff . |
| 4,307,722 | 12/1981 | Evans . |
| 4,323,071 | 4/1982 | Simpson et al. . |
| 4,327,709 | 5/1982 | Hanson et al. . |
| 4,349,033 | 9/1982 | Eden . |
| 4,444,188 | 4/1984 | Bazell et al. . |
| 4,515,587 | 5/1985 | Schiff . |
| 4,540,404 | 9/1985 | Wolvek . |
| 4,545,390 | 10/1985 | Leary . |
| 4,561,439 | 12/1985 | Bishop et al. . |
| 4,582,181 | 4/1986 | Samson . |
| 4,614,188 | 9/1986 | Bazell et al. . |
| 4,638,805 | 1/1987 | Powell . |
| 4,646,719 | 3/1987 | Neuman et al. . |
| 4,646,742 | 3/1987 | Packard et al. . |
| 4,655,748 | 4/1987 | Mushika . |
| 4,715,378 | 12/1987 | Pope, Jr. et al. . |
| 4,719,924 | 1/1988 | Crittenden et al. ................. 128/772 |
| 4,771,778 | 9/1988 | Mar .................................... 128/344 |

OTHER PUBLICATIONS

Advanced Cardiovascular Systems literature, Low--Profile Steerable Catheter, 10/83.
The USC/Bard literature, USCI Probe PTCA Dilation System, 10/87.

Primary Examiner—Stephen C. Pellegrino
Attorney, Agent, or Firm—Fish & Richardson

[57] ABSTRACT

Dilation balloon devices that employ a metal tube for introduction of inflation fluid from distal end into a balloon have special features that enable introduction through very small passages. A distal core wire is shown forming part of a guide wire extending into the distal end of the tube. The core wire is fixed at the distal end of the tube, and has a proximal extension bridging across a fluid opening formed in the wall of the tube. The wire extension serves to transfer stress from the distal end of the device, across the fluid opening, to adjacent proximal portions of the tube, to prevent stress build-up at the opening that might lead to fracture of the tube during bending. In various embodiments, the device includes a bushing seal at the distal end of the balloon; a helical coil surrounds part or all of the length of the device, with strategic tapers along its length; a shrink tubing is used rather than a coil; and a pair of cross-wound multifilar coils are employed. A balloon having a very thin wall, even in its transition section, is formed from a specially prepared tubular preform.

21 Claims, 8 Drawing Sheets

DILATION BALLOON

This application is a continuation-in part of U.S. Ser. No. 126,769, filed Nov. 30, 1987.

BACKGROUND OF THE INVENTION

The invention relates to dilatation balloon devices which are introduced into body passageways for the purpose of dilating a collapsed portion of the passageway. In particular, the invention provides devices capable of use in balloon angioplasty.

Typically, the balloon, placed at the distal end of a flexible shaft, enters the body by means of a catheter. The balloon is then positioned in the affected region and inflated, thereby forcing the obstructed way open. The balloon may then be deflated and the device withdrawn back through a catheter and from the body.

It is advantageous for such devices to provide a small diameter profile when the balloon is deflated to allow atraumatic advance through body passageways and for positioning the balloon in the region of narrowing lesions. Angioplasty of smaller arteries, such as the coronary artery, typically requires balloons of 3 mm inflated diameter or less, which, when deflated and collapsed about a shaft, can be introduced through diagnostic catheters. For larger arteries, such as the renal artery or popliteal artery, balloons of larger inflated diameter, up to as large as 8 mm, are required for angioplasty treatment; the lesions of these arteries, however, are not necessarily larger. Larger balloons, when deflated, tend to produce larger diameter profiles, thereby inhibiting their use across narrow lesions and requiring larger diameter introduction catheters.

SUMMARY OF THE INVENTION

According to one aspect of the invention, a dilatation balloon device comprising an inflatable balloon, and a main tubular member comprising a metal tube having distal and proximal ends, and adapted for introduction of inflation fluid from its distal end into the balloon, a distal core wire forming part of a guide wire extends into the distal end of the tube, the wire being fixed at the distal end of the tube and having a proximal extension bridging across a fluid opening defined in the wall of the tube, the wire extension serving to transfer stress from the distal end of the device, across the fluid opening, to proximally adjacent portions of the tube, thereby to prevent stress build-up at the opening that might lead to fracture of the tube during bending of the device.

In the preferred embodiment, the device further comprises a balloon sleeve extending proximally of an expandible portion of the balloon, across the fluid opening to a point of attachment to the tube.

According to another aspect of the invention, a dilatation balloon device capable of being placed through a conventional 5 French diagnostic catheter and capable of supporting a balloon having an inflated diameter up to about 8 mm diameter comprises an inflatable balloon having a proximal and a distal end, the balloon being the product of the process of blowing and drawing a preformed tubular member having a tapered contour in the region corresponding to the transition section of the blown balloon, a flexible elongated, torque transmitting hollow main tubular body of outside diameter of 0.038 inch or less, extending from a proximal region of the device to a position spaced from a distal end of the deice, the main tubular body having a distal portion and defining an interior volume adapted to conduct inflation liquid for the balloon, flexible spanning structure extending distally from the end of the main tubular body, the spanning structure defining a fluid passage for communication between the distal portion of the main tubular body and the balloon, and including a torque-transmitting element that extends from the main tubular body to a sealing formation at the distal end of the balloon, the portion of the spanning structure that corresponds with the length of the balloon having an outer diameter no greater than about 0.025 inch, enabling the balloon to be collapsed to a profile of about 0.038 inch diameter or smaller, the effective outer diameter of the spanning structure at the sealing formation being about 0.025 inch, to which a distal sleeve of the balloon is joined, and a flexible, torqueable guide element extending distally from the sealing formation to the end of the device.

Preferred embodiments of this aspect of the invention may include one or more of the following features. The hollow main tubular body includes a hollow metal tube, the torque transmitting element comprises a solid cross-section core wire joined to the distal end of the main tubular body and extending through the balloon to the sealing formation, the sealing formation including a solid annular member sealed to the wire for providinq support for a distal sleeve of the balloon of substantially larger diameter than the wire. A helical coil is joined to an outer surface of the sealing formation and extends distally therefrom to provide a flexible distal tip, the sleeve of the balloon being joined to an outer surface of the helical coil at the sealing formation. The hollow main tubular body includes a hollow metal tube, the torque transmitting element comprises a solid cross-section core wire joined to the distal end of the main tubular body and extending through the balloon to the sealing formation, and wherein the main tubular member has a first outer diameter for most of its length and a second, reduced outer diameter portion at its distal end, the inner diameter of a region of the second, reduced outer diameter corresponding to the outer diameter of the core wire over a joint region at which the main tubular member and the solid cross-section wire are joined, the main tubular member having a fluid opening proximal of the joint region and the solid cross-section wire having a proximal portion spanning across the opening and extending proximally thereof, adapted to transfer stress from distal of the main tubular member to a portion of the main tubular member proximal of the opening, there being a flow path for inflation fluid to the opening within the main tubular member in a space defined at its inner periphery by an external surface of a proximal portion of the solid cross-section wire.

According to another aspect of the invention, a dilatation balloon device comprises an inflatable balloon, a flexible elongated, torque transmitting hollow metal main tubular body extending from a proximal region of the device to a position spaced substantially from a distal end of the device, the main tubular body defining an interior volume adapted to conduct inflation liquid for the balloon, flexible spanning structure extending distally from an end of the main tubular body, the spanning structure defining a fluid passage for communication between a distal portion of the main tubular body and the balloon, and including a torque-transmitting element that extends from the main tubular body to a distal end of the balloon, the torque transmitting element comprising a solid cross-section core wire joined to a distal end of the main tubular body and extending through the balloon, the main tubular member having a first outer diameter portion for most of its length and a second, reduced outer diameter portion at its distal end, an inner diameter of the second, reduced outer diameter portion corresponding to the outer diameter of he wire over a joint region at which the member and wire are joined, the tubular member having a fluid opening proximal of the joint region and the wire having a proximal portion spanning across the opening and extending proximally thereof, adapted to transfer stress from distal of the main tubular member to a portion of the main tubular member proximal of the opening, there being a flow path for inflation fluid to the opening within the tubular main body in a space defined at its inner periphery by an external surface of a proximal portion of the core wire.

Preferred embodiments of this and the other aspects of the invention may include one or more of the following features. The main tubular member tapers from the first outer diameter portion to the second, reduced outer diameter portion at its distal end. The wire extends to a distal tip of the device, the distal portion of the wire being of reduced diameter and more flexible relative to proximal portions thereof. Helical coil means extend from the proximal region to the distal end of the device. A helical coil extends over a hollow liquid-tight tube from the proximal region of the device to the distal region of the main tubular body and a fluid impermeable sleeve extends from the distal region of the tubular body to the balloon. Flexible polymeric tube means extend from the proximal region of the device to the proximal portion of the balloon. The main tubular body comprises an exterior heat shrink tube shrunk upon a hollow metal liquid-conducting tube. The balloon is the product of the process of blowing and drawing a preformed tubular member having a tapered contour in the region corresponding to the transition section of the blown balloon. The preformed tubular member is the product of heating and drawing a defined region of an extruded tube of originally constant diameter and wall thickness. The wall thickness of the tapering transition section is about the same as the wall thickness of the main body of the balloon. The wall thickness of the tapering transition section is less than the wall thickness of the main body of the balloon. The main body of the balloon has an inflated diameter of 5 mm or larger. The resin from which the balloon is formed is polyethylene terephthalate (PET). An elongated sleeve extending proximally from the balloon past the inflation opening is formed integrally with the balloon as a result of drawing the tubular member. The balloon has sleeves of smaller diameter than the original diameter tube from which the sleeves are formed.

According to another aspect of the invention, a dilatation balloon device comprises an inflatable balloon, a main tubular member comprising a metal tube having distal and proximal ends, and adapted for introduction of inflation fluid from its distal end into the balloon, and a flexible spanning structure comprising concentric cross wound multifilar coils extending from the end of the hollow main tubular body to the distal end of the balloon.

The invention thus provides a balloon dilatation construction for a range of balloon sizes which has a minimum diameter deflated profile such that it may be introduced through a very small diameter catheter.

These and other features and advantages of the invention will be seen from the following description of a presently preferred embodiment, and from the claims.

PREFERRED EMBODIMENTS

We first briefly describe the drawings.

Drawings

FIG. 2 is an enlarged partial side section view of the distal end of the metal tube used in the device, while

FIG. 2b is a view similar to FIG. 2 but under the condition that the dilatation device is bent, while

DETAILED DESCRIPTION

Figure 1:
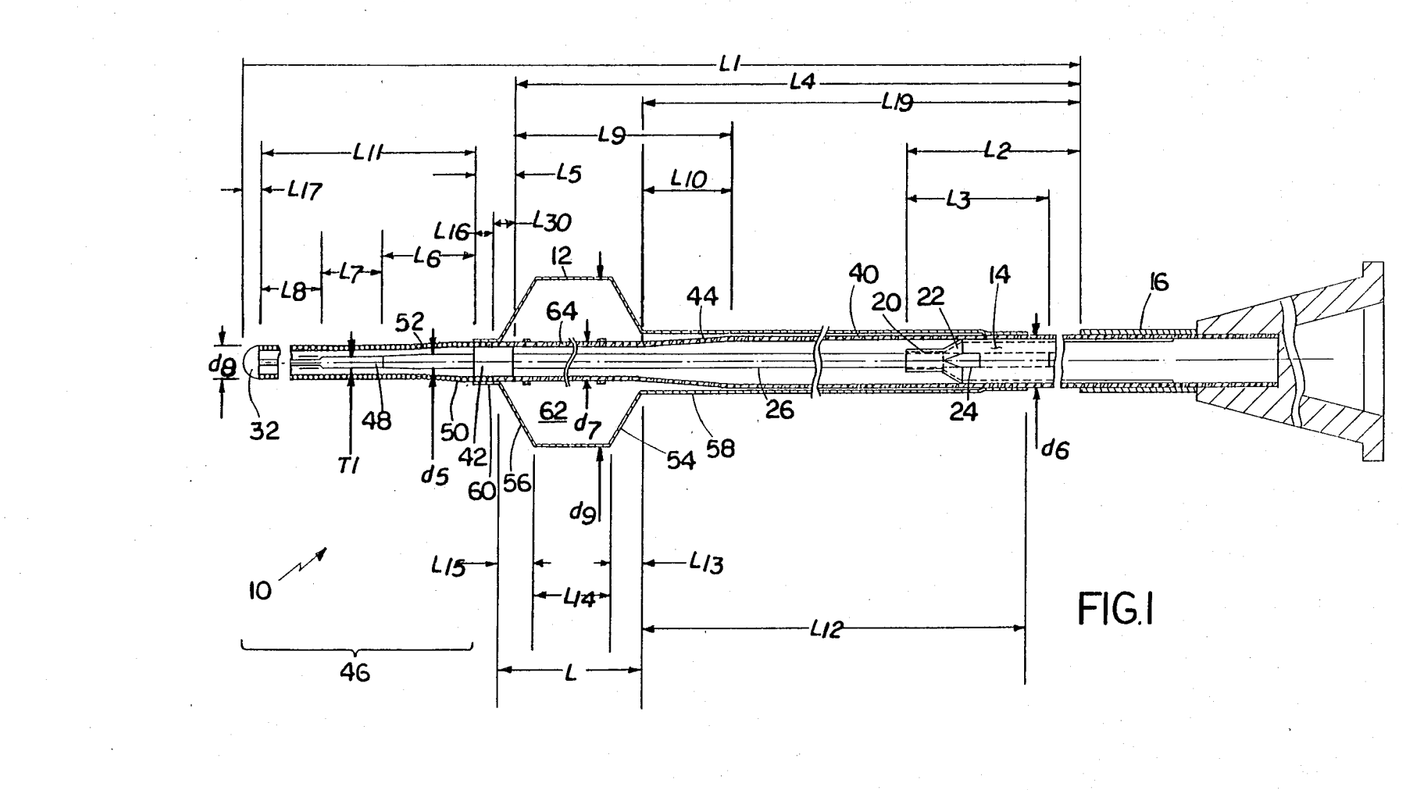
FIG. 1 is a side section view of a dilatation device according to the invention having a wire coil that extends from the proximal end to the distal end of the balloon.

The dilatation device 10, shown in FIG. 1, has length $L_1$, e.g. 100 cm, with a dilatation balloon 12 positioned close to the distal end. The device employs hollow metal tube 14, which extends length $L_2$, e.g. 85 cm, in the distal direction from a strain relief 16 on a luer fitting 18. The main proximal body of tube 14 has an outer diameter $d_1$, e.g. 0.025 inch, and an inner diameter $d_2$, e.g. 0.021 inch. A short distal portion 20 of tube 14 is swaged to a smaller diameter, which may be seen most clearly in FIG. 2. This portion has an outer diameter $d_3$, e.g. 0.016 inch, and an inner diameter $d_4$, e.g. 0.011 inch, and extends for length $L_{18}$, e.g. 4 mm, in the proximal direction until meeting a swaged transition taper 22. The taper extends axially for length $L_{20}$, e.g. 2 mm, integrally joining the main body to the smaller distal portion 20 of the tube. An inflation opening 24 in the wall of the tube extends for length $L_o$, e.g. 4 mm, in the proximal direction from the distal end of the taper 22.

Figure 2:
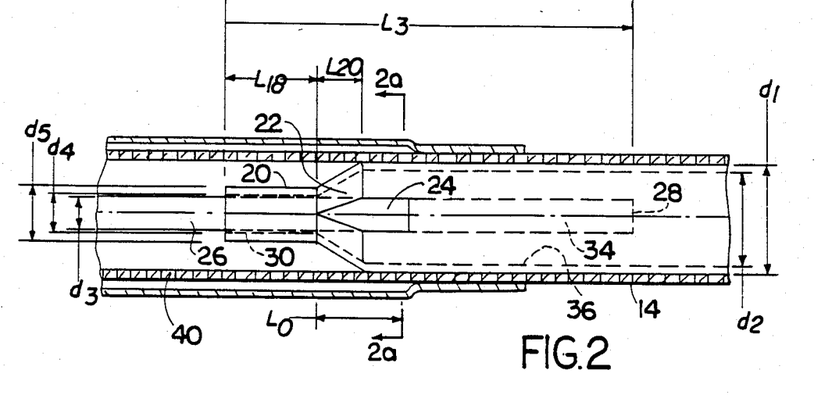

A core wire 26 of diameter $d_5$, e.g. 0.010 inch, is inserted in the reduced distal end 20 of the tube 14, and protrudes past opening 24 into the main body of the tube 14 by a distance $L_3$, e.g. about 15 mm, from the distal end of tube 14, to a free end 28. In the reduced region 20, this wire is soldered at 30 to the tube 14. The proximal extension 34 of the wire spans the inflation opening while leaving it unobstructed. The core wire 26 extends distally beyond the tube 14 to the distal end of the device, terminating at a ball weld 32.

Figure 2A:
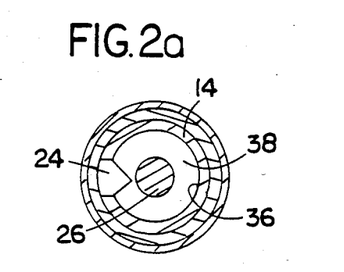
FIG. 2a is a sectional view of the device taken at line 2a—2a of FIG. 2.
Figure 2B:
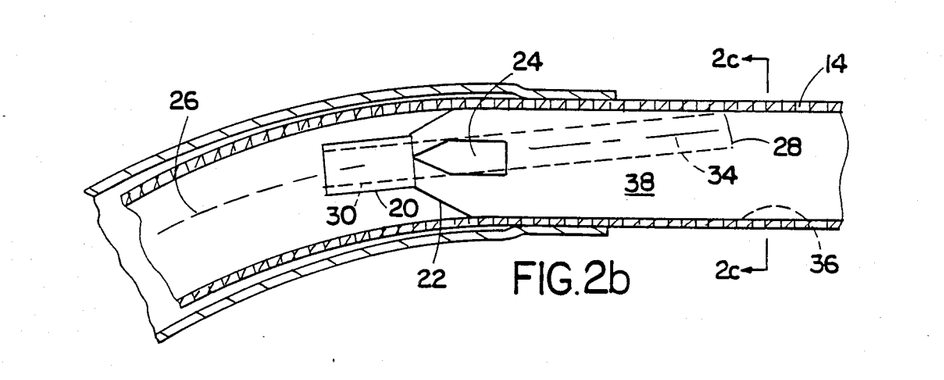
Figure 2C:
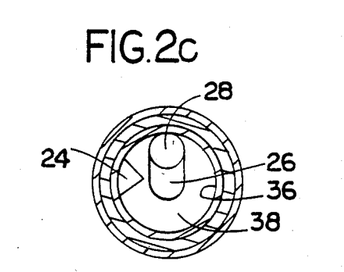
FIG. 2c is a sectional view similar to FIG. 2a taken on line 2c—2c of FIG. 2b.

Referring to FIG. 2a, the proximal extension 34 of core wire 26 defines, with the inner wall 36 of the tube, an annular orifice 38 for passage of inflation medium (typically a viscous liquid which includes a contrast medium) about the core wire, and out of the tube via inflation opening 24. When the distal tip portion of the dilatation wire 10 is flexed, e.g., to negotiate a passage of tight radius within the body, the core wire 26 is secure at the solder joint 30 with the reduced tube portion 20. At a predetermined bending radius, dependent upon the relationship of length $L_3$ and diameters $d_2$ and $d_3$, the free end 28 of the core wire bears upon the inner wall 36 of the tube (FIGS. 2b and 2c) causing transfer to the tube wall of bending stress applied to the distal tip, thereby preventing detrimental stress build-up in the region of the opening or the solder joint.

A helical wire coil 40 is provided concentrically about the tube 14 and the core wire 26. The coil 40 is preferably made from 0.004 inch×0.008 inch flat wire and extends from under the strain relief 16 of the luer fitting to a bushing or seal 42 of length $L_5$, e.g. 2 mm, at the distal end of the balloon 12 at which point the distal end of the coil 40 is soldered. The coil includes a tapered region 44 in its distal portion approaching the position of the balloon, extending distally for length $L_{10}$, e.g. 2 cm, in which the outer diameter of the coil is reduced from $d_6$, e.g. 0.034 inch, to $d_7$, e.g. 0.025 inch. Between the taper 44 and the bushing or seal 42, the coil has an outer diameter of about 0.025 inch.

Figure 3:
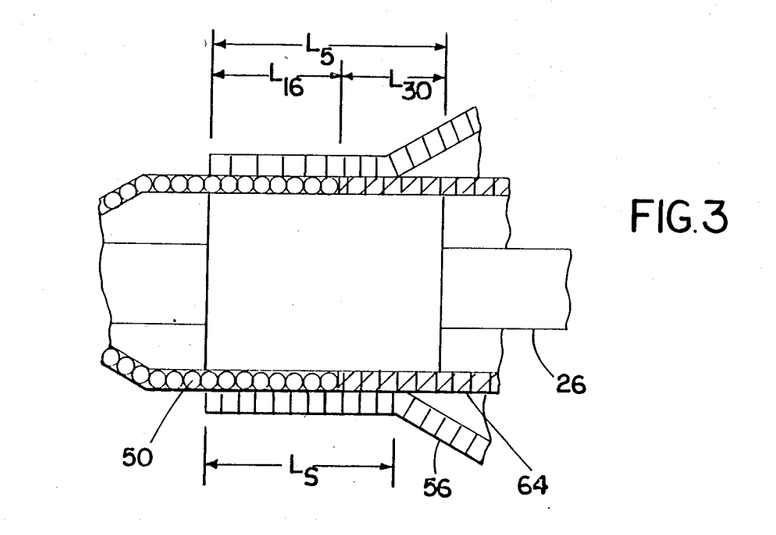
FIG. 3 is an enlarged partial side view of a bushing of the device.

A highly flexible distal tip region 46 is provided at the distal end of the device which includes the core wire 26, tapered in region 48 after it emerges from the bushing 42, such that the outer diameter is reduced from $d_3$, e.g. 0.010 inch, to $d_5$, e.g. 0.006 inch, over an axial length of 1 cm. Distal to the taper follows a region $L_7$, e.g. 0.5 cm in length, of constant diameter which is in turn followed distally by a region $L_8$, e.g. 1.5 cm in length, which is flattened to a thickness $T_1$, e.g. 0.003 inch, and terminates at the distal ball weld 32. Disposed concentrically about the core wire distal to the bushing is a distal coil 50, constructed from 0.003 inch platinum round wire (selected for improved viewability due to its relatively high radiopacity) and soldered over the distal length $L_{16}$, e.g 2 mm, of the bushing 42. Distal to the bushing 42, the coil 50 tapers at 52 such that the outer diameter is reduced from 0.025 inch at the proximal end to $d_8$, e.g. 0.018 inch, at the distal end where it meets the ball weld 32. (The taper may begin immediately distal of the bushing, or more typically 3-4 coils after the bushing, as seen in FIG. 3. In other embodiments, the bushing 42 may also taper distally.) Other embodiments for the flexible tip include terminating the core wire at the bushing and employing a high tensile strength polymeric filament, such as Kevlar ® or a safety wire distal to the bushing.

The bushing or seal 42, shown in detail in FIG. 3, is preferably a stainless steel tube of axial length $L_5$, e.g. 4 mm, and 0.025 inch outer diameter, with a through hole diameter approximately equal to the outer diameter $d_5$ of the core wire 26. The outer diameter of the bushing may be selected to permit the use of relatively large balloons with relatively large sleeves. The bushing further serves to ensure a strong union between the distal end of proximal wire coil 40 and the proximal end of the extension coil 50, and also provides a seal to flow of inflation fluid from the balloon.

The device further includes an extremely thin and tightly collapsible inflatable balloon 12, the manufacture of which is described in detail below. The balloon features proximal and distal transition sections 54 and 56 having wall thickness about the same as that of the largest dilatating region of the balloon, and proximal and distal sleeves 58 and 60 which fix the balloon to the shaft. The proximal sleeve 58 is of considerable length $L_{12}$, e.g. 15 cm. The distal sleeve 60 extends distally a distance $L_5$, e.g. 4 mm, and is fixed and sealed to the proximal coil 44 and distal coil 50 at a position over the bushing 42. The balloon is positioned on the device such that the region of maximum inflated diameter 62 corresponds to the reduced diameter region 64 of the coil 40. When the balloon 12 is deflated, the device 10 has a maximum diameter of 0.039 inch, thereby allowing insertion in places where a conventional 0.038 inch diameter guide wire may be inserted.

During use, the device is inserted into an artery, e.g., via a 5-French diagnostic catheter. The flexible distal tip 46 allows atraumatic advance through tortuous body passages and permits placement at narrowing lesions. The core wire 26, coil 40 and tube 14 give structural integrity together with flexibility and torqueability which permits advance of the device of the invention without kinking when applying force and twisting from its distal end. During bending, stress in the region of the distal portion of the tube is transferred across its narrow diameter portion 20 and taper 22 by the proximal extension 34 of the core wire 26, as mentioned above. Once positioned at a lesion, the balloon 12 is inflated by introducing fluid from the proximal end of the tube 14. The fluid flows through inflation port 24 and the coil 40. The balloon, sealed by its sleeves at the distal bushing 42 and at the main shaft proximal to the inflation port 24, is thereby inflated.

Figure 4:
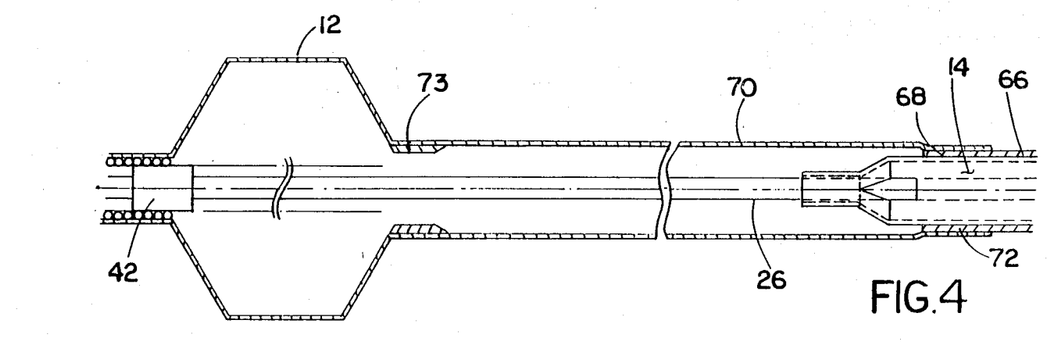
FIG. 4 is a partial side section view of another embodiment of the invention in which the main wire coil terminates at the distal end of the inflation tube and a sleeve spans the structure over the core wire to the balloon.

In another embodiment of the invention, shown in FIG. 4, a wire coil 66 extends from the proximal region of the tube 14 to an end 68 near the distal end of the main body of the tube. A separately formed, extended sleeve 70, preferably 0.004 inch thick and formed from a structurally strong resin such as polyethylene terephthalate (PET), is sealably fixed to the distal region of the coil at 72 and is joined to the proximal sleeve of balloon 12 at its proximal end 73, alternatively the sleeve is formed integrally with the balloon, see below.

Figure 5:
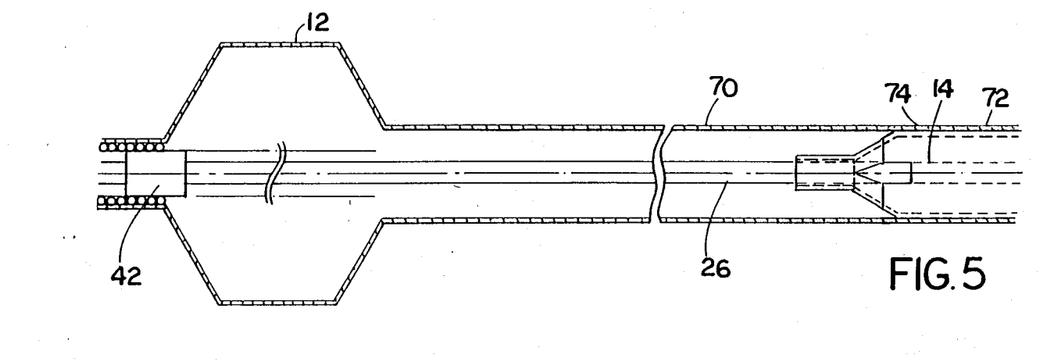
FIG. 5 is a partial side section view of another embodiment of the invention in which a polymer shrink tubing covers the metal tube, terminating at its distal end and a sleeve spans the structure over the core wire to the balloon.

In another embodiment of the invention, shown in FIG. 5, a heat shrinkable polymer tubing 72, such as Teflon ®, is shrunk onto tube 14. The shrink tubing extends from the proximal end of the device and terminates about the distal portion of the tube 14. The most distal portion 74 of shrink tubing 72 includes a thin wall region to which a PET sleeve 70 is sealably fixed, as in FIG. 4.

Figure 6:
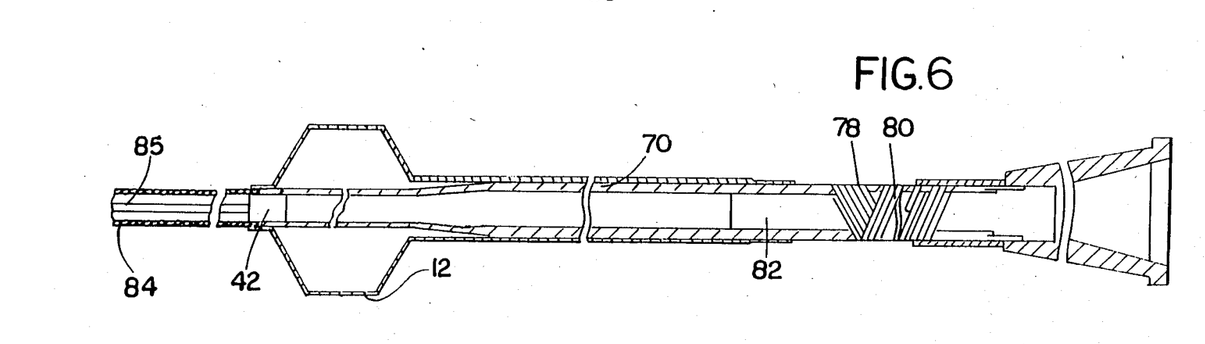
FIG. 6 is a partial side section view of another embodiment of the invention in which a cross-wound pair of multifilar coils is employed.

Another embodiment of the device, shown in FIG. 6, includes a pair of cross wound multifilar coils 78, 80, preferably wound from 0.002 inch wire extending from the proximal portion of a tube 82 to the distal end of a flexible distal tip 84 of the device. Due to the superior strength and torque transmission characteristics of the multifilar coils, no core wire or safety wire is required in the region of the balloon. (In the embodiment shown, the distal tip region is a platinum coil, as described above, and a core or safety wire 85 extends from bushing or seal 42 to the ball weld tip. If the distal tip region is formed of, e.g., of a multifilar coil, no core or safety wire may be necessary.)

In the preferred embodiment, the balloon of FIG. 1 is manufactured by a process of heating and drawing a defined region of an extruded tube of originally constant diameter and wall thickness; the main body section and the tapering transition section of the balloon have substantially the same wall thickness or the transition section is thinner; the main body of the balloon has an inflated diameter of 5 mm or larger; and the resin from which the balloon is formed is polyethylene terephthalate (PET).

Figure 7:
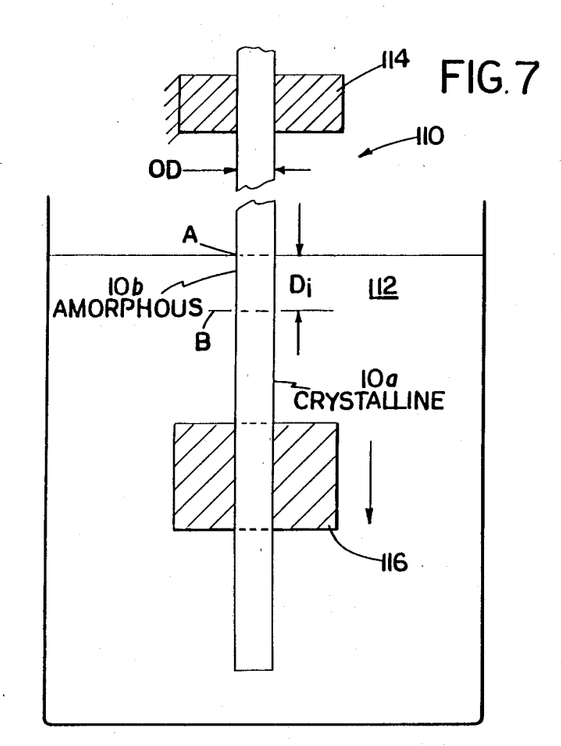
FIG. 7 is a diagrammatic view of an extrusion-formed tubular element of a selected resin material being heated and drawn as a step of the present invention.
Figure 7A:
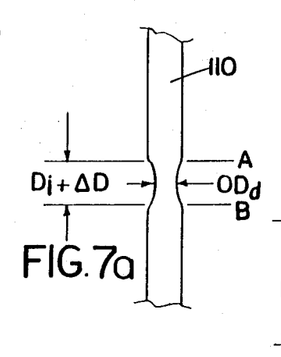
FIG. 7a is a diagrammatic view of a drawn section of the tubular element.
Figure 7B:
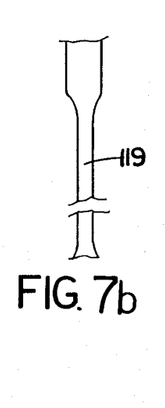
FIG. 7b is a view similar to 7a of another form with an elongated necked-down region.

Referring to FIG. 7, a tube suitable for blowing a medical balloon of 6 mm diameter is provided, comprised of a nondistendable resin, e.g. Goodyear's Clear Tuf 8006, polyethylene terephthalate, having an outer diameter of 0.066 inch and a wall thickness of 0.011 inch. A portion 10a of the tube, up to line B, has been crystallized to render it dimensionally stable under heated conditions. The portion thus stabilized can not be appreciably inflated or drawn. The tube 110 is immersed in a heated bath 112 of glycerine at a selected drawing temperature in the range of about 105 to 130 degrees centigrade, e.g., 120° C. The crystallized region is fully immersed together with a short portion, $D_{11}$, e.g. 3 mm, of the amorphous portion 10b of the tube. The portion of the tube out of the bath is gripped by a fixed clamp 114, and the crystallized portion of the tube submerged in the bath is gripped by a moveable clamp 116. After a suitable duration of immersion, to ensure that the resin reaches the temperature of the bath, clamp 116 is moved downwardly a predetermined distance, e.g. 2 mm, at a draw rate in the range of about one inch to 0.1 inch per minute e.g. 0.3 inch per minute, in the direction of the arrow, causing the heated amorphous portion of the tube to be drawn, the crystallized portion resisting such deformation. Referring to FIG. 7a, a tube 110, in the region between A and B as shown in FIG. 7, is necked-down as a result of such drawing. The degree of necking and thinning of the walls obviously depends upon the conditions of drawing, e.g., the drawing rate, drawing temperature, length of the amorphous portion being drawn and the distance of draw, the values of which for any particular balloon can be determined by ready trial. In the embodiment being described, the outer diameter of the tube $OD_d$ is necked to 0.054 inch and the tube is lengthened 2 mm. In the preferred embodiment of FIG. 7b for use in FIG. 1, a longer portion of the amorphous tube has been immersed, and the tube is drawn down to a constant diameter sleeve 119 for use as the proximal elongated, integral sleeve in the completed device of the invention. (In the embodiment of FIG. 4, the sleeve 70 is formed separately, as a tube of PET in amorphous state is glued to the proximal end of the balloon (at 73) and crystallized to render it dimensionally stable under heated conditions to resist inflation or drawing.)

Figure 7C:
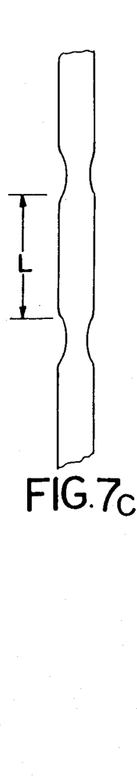
FIG. 7c is a view on a smaller scale showing the entire preform with two necked-down regions separated by a distance L.

After the initial necking-down of the tube, the tube is reversed in the bath and the second necked-down portion is formed by the same procedure, at a point spaced along the amorphous tube a distance L, e.g. 0.57 inch, to provide a section of tube between the necked-down regions which will be drawn and blown in forming the main body of the balloon. This procedure provides a preform in which the thickness of the wall of the tube in the region of the drawn-down deformation decreases with decrease in diameter.

Figure 8:
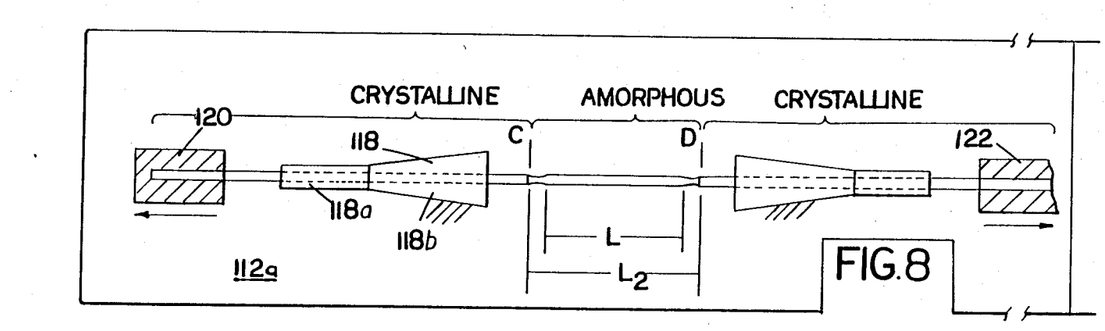
FIG. 8 is a diagrammatic view of the preform of FIG. 7c in a position ready to be blown into a balloon.

After the preform is completed, it is submerged in a second bath of glycerine as shown in FIG. 8, this time arranged horizontally, and with the tube extending through two stationary constraining elements 118, the crystallized portion of the tube being grasped by clamps 120, 122. The temperature of bath 112a is regulated to correspond to the desired blowing temperature, selected from the range of about 85 to 115 degrees centigrade. Each constraining element 118 is comprised of a cylindrical portion 118a and a conical portion 118b, the wide ends of the conical portions being opposed to each other, arranged to define the shape of the tapered sections of the balloon.

Figures 9, 9A:
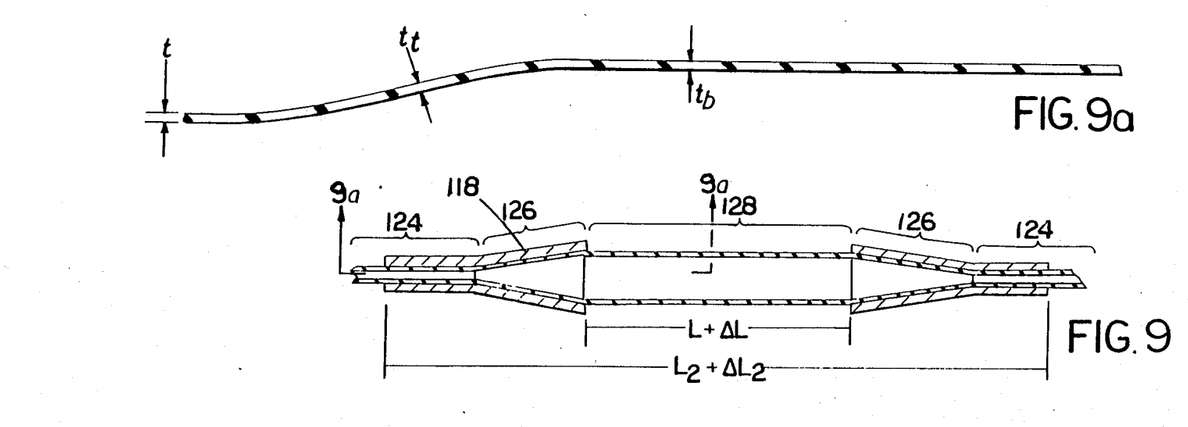
FIG. 9 is a view similar to FIG. 8 but in cross-section showing the formed balloon.
FIG. 9a is a cross-section of the wall of the balloon of FIG. 9 showing the generally uniform wall thickness achievable along the length of the tube.

As shown, the crystallized regions of the tube end at points C and D in the initial setup of FIG. 8. After the temperature of the tube has stabilized in bath 112a, the two clamps 120 and 122 are drawn apart, causing the tube to slide through the stationary constraining elements 118 as it is lengthened. Simultaneously, gas pressure is applied to the interior of the tube, causing it to expand. The region L of the tube expands without constraint until the molecules of the wall material in the balloon region become stabilized in a biaxially oriented condition. In its final form, the balloon reaches an outer diameter of 8 mm and the length between the tapered sections increases to $L + \Delta L = 1.51$ inches. The portions of the tube having the preformed tapers also expand until they are constrained to the shape of constraining elements 118. The final balloon thickness profile is illustrated in FIG. 9a in which the thickness of the balloon $t_b$ is 0.0007 inch and the thickness $t_t$ of the tapered wall is substantially of the same value with variation less than about 0.0001 inch. The length of the amorphous region during the blow and draw step increase from $L_2 = 0.94$ inch to $L_2 + \Delta L_2 = 2.70$ inch.

It is also possible in forming the preform, e.g., by drawing more on the defined region, and thus drawing the taper down further, to achieve in the blown balloon a wall thickness of the transition region that is less than that of the main body of the balloon.

Figures 10, 11:
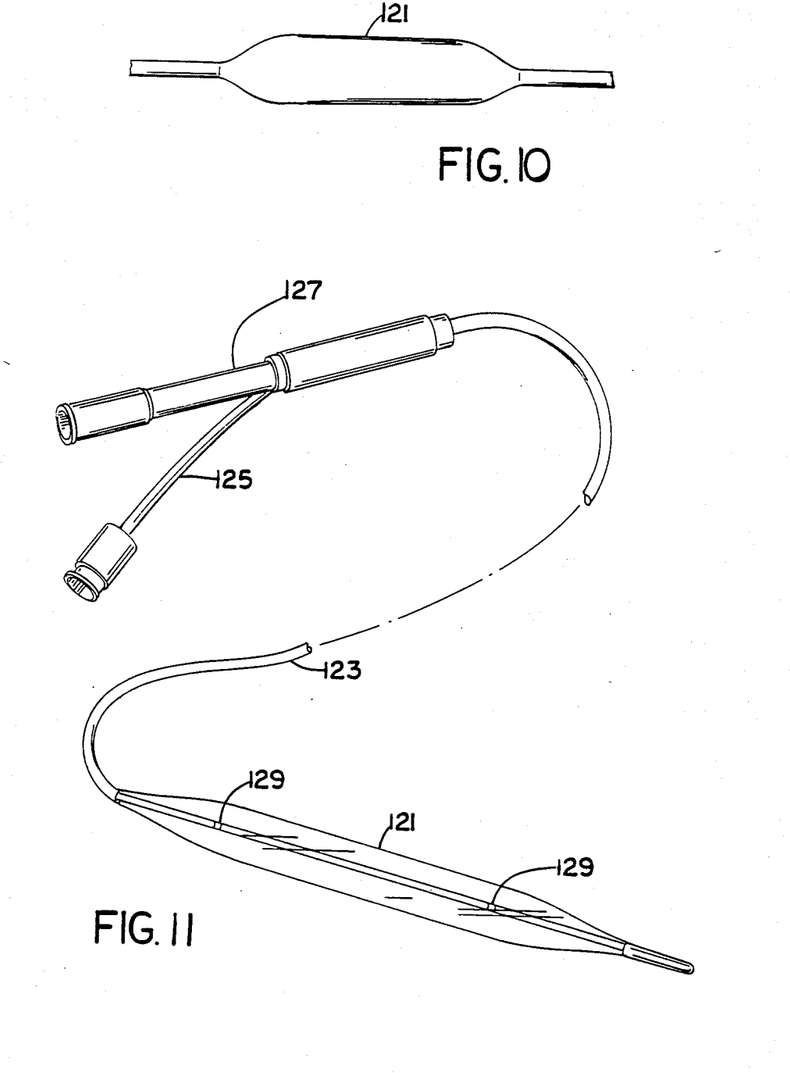
FIG. 10 is a side view of a finished balloon produced according to the invention.
FIG. 11 is a similar view of an angioplasty balloon catheter according to the invention.

After formation of the balloon, the balloon is cooled, dried, the end portions are cut away, and the balloon 121 is assembled upon the previously assembled shaft. Radiopaque markers 129 are provided on the catheter at the ends of the main body of the balloon 121. In this manner, a large balloon, e.g. of 6 to 8 mm diameter, capable of pressures of, e.g., 8 atmospheres, can be obtained, having transition regions that are sufficiently thin to enable atraumatic collapse. The balloon is capable of very successful dilation on a device which may be passed through a very small introduction catheter.

A particular advantage is obtained when making the larger balloon sizes for assembly on small shafts, for instance an 8 mm balloon for the shafts described above.

To form such a balloon, it is advantageous to choose a starting tube of diameter greater than the outer diameter of the shaft on which the balloon is ultimately to be mounted. By use of the drawing steps to form the preform, it is readily possible, in the defined heated regions, to draw the diameter of these regions to a size corresponding to the size of the shaft.

Figure 12:
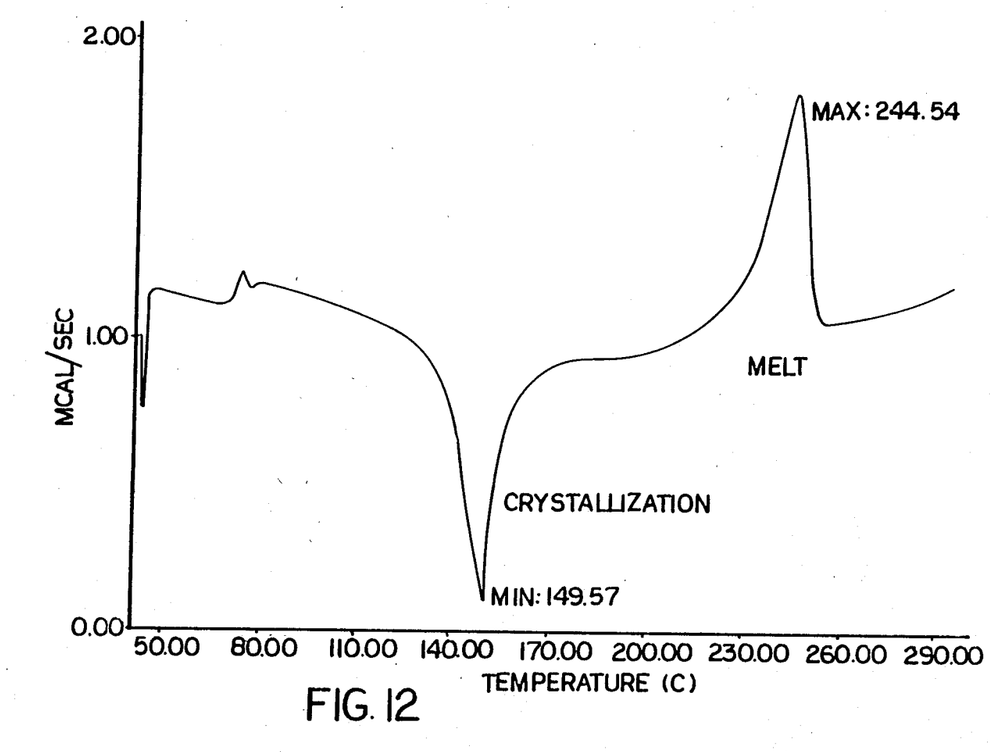
FIG. 12 is a thermal analysis curve of PET resin, a material suitable for forming a device of the invention.

In various embodiments, the wall thickness of the tapered section can be increased or decreased according to the amount of draw performed during fabrication of the preform. In some embodiments, use of constraining elements in the end regions may be omitted, and in other embodiments the entire preform may be confined in a mold for determining the final blown shape. The temperature in other embodiments may be outside of the preferred ranges mentioned, provided certain relationships are maintained, see above, with reference to the thermal analysis curve for the respective resin (see the example for the preferred embodiment, FIG. 12, a thermal analysis curve for polyethylene terephthalale (PET), one preferred resin).

For certain of the broader aspects of the invention, other forming techniques such as molding of a softened tube are possible for preparing the tapered preform.

What is claimed is:

1. In a dilatation balloon device comprising an inflatable balloon, and a main tubular member comprising a metal tube having distal and proximal ends, said inflatable balloon disposed adjacent the distal end of said main tubular member and in fluid flow connection therewith, said main tubular member adapted for introduction of inflation fluid from its distal end into said balloon, a distal core wire forming part of a guide wire having a proximal end portion extending into the distal end of the tube, and a distal end portion extending within said balloon to a distal termination, said wire being fixed at the distal end of the tube and having a proximal extension bridging across a fluid opening defined in the wall of the tube, the wire extension serving to transfer stress from the distal end of the device, across the fluid opening, to proximally adjacent portions of the tube, thereby to prevent stress build-up at the opening that might lead to fracture of the tube during bending of the device.

2. The dilatation balloon device of claim 1 further comprising a balloon sleeve extending proximally of an expandible portion of said balloon, across said fluid opening to a point of attachment to the tube.

3. A dilatation balloon device capable of being placed through any catheter that accepts an 0.038 inch diameter wire and capable of supporting a balloon having an inflated diameter up to about 4 mm diameter, said device comprising:

an inflatable balloon having a proximal and a distal end, said balloon being the product of the process of blowing and drawing a preformed tubular member having a tapered contour in the region corresponding to the transition section of the blown balloon, a flexible elongated, torque transmitting hollow main tubular body of outside diameter of 0.038 inch or less, extending from a proximal region of the device to a position spaced from a distal end of the device, said inflatable balloon disposed adjacent the distal end of said main tubular member and in fluid flow connection therewith, said main tubular body having a distal portion and defining an interior volume adapted to conduct inflation liquid for said balloon, flexible spanning structure extending distally from the fluid passage for communication between the distal portion of said main tubular body and the balloon, and including a torque-transmitting element that extends that extends from the main tubular body to a sealing formation at the distal end of the balloon, the portion of said spanning structure that corresponds with the length of the balloon having an outer diameter no greater than about 0.025 inch, enabling the balloon to be collapsed to a profile of about 0.038 inch diameter or smaller, the effective outer diameter of said spanning structure at said sealing formation being about 0.025 inch, to which a distal sleeve of the balloon is joined, and a flexible, torqueable guide element extending distally from said sealing formation to the end of the device.

4. The dilatation balloon device of claim 3 wherein said hollow main tubular body includes a hollow metal tube, said torque transmitting element comprises a solid cross-section core wire joined to the distal end of said main tubular body and extending through said balloon to said sealing formation, said sealing formation including a solid annular member sealed to said wire for providing support for a distal sleeve of said balloon of substantially larger diameter than said wire.

5. The dilatation balloon device of claim 3 wherein a helical coil is joined to an outer surface of said sealing formation and extends distally therefrom to provide a flexible distal tip, the sleeve of the balloon being joined to an outer surface of said helical coil at said sealing formation.

6. The dilatation balloon device of claim 3 wherein said hollow main tubular body includes a hollow metal tube, said torque transmitting element comprises a solid cross-section core wire joined to the distal end of said main tubular body and extending through said balloon to said sealing formation, and wherein said main tubular member has a first outer diameter for most of its length and a second, reduced outer diameter portion at its distal end, the inner diameter of a region of the second, reduced outer diameter corresponding to the outer diameter of the core wire over a joint region at which said main tubular member and said solid cross-section wire are joined, said main tubular member having a fluid opening proximal of said joint region and said solid cross-section wire having a proximal portion spanning across said opening and extending proximally thereof, adapted to transfer stress from distal of said main tubular member to a portion of said main tubular member proximal of said opening, there being a flow path for inflation fluid to said opening within said main tubular member in a space defined at its inner periphery by an external surface of a proximal portion of said solid cross-section wire.

7. A dilatation balloon device comprising;
   an inflatable balloon,
   a flexible elongated, torque transmitting hollow metal main tubular body extending from a proximal region of the device to a position spaced substantially from a distal end of the device, said inflatable balloon disposed adjacent the distal end of said main tubular member and in fluid flow connection therewith, said main tubular body defining an interior volume adapted to conduit inflation liquid for said balloon, flexible spanning structure extending distally from an end of said main tubular body, said spanning structure defining a fluid passage for communication between a distal portion of said main tubular body and the balloon, and including a torque-transmitting element that extends from the main tubular body to a distal end of the balloon, said torque transmitting element comprising a solid cross-section core wire joined to a distal end of said main tubular body and extending through said balloon, said main tubular member having a first outer diameter portion for most of its length and a second, reduced outer diameter portion at its distal end, an inner diameter of the second, reduced outer diameter portion corresponding to the outer diameter of the wire over a joint region at which said member and wire are joined, said tubular member having a fluid opening proximal of said joint region and said wire having a proximal portion spanning across said opening and extending proximally thereof, adapted to transfer stress from distal of said main tubular member to a portion of said main tubular member proximal of said opening, there being a flow path for inflation fluid to said opening within said tubular main body in a space defined at its inner periphery by an external surface of a proximal portion of said core wire.

8. The dilatation balloon device of claim 6 or 7 wherein said main tubular member tapers from said first outer diameter portion to said second, reduced outer diameter portion at its distal end.

9. The dilatation balloon of claim 1, 6 or 7 wherein said wire extends to a distal tip of said device, the distal portion of said wire being of reduced diameter and more flexible relative to proximal portions thereof.

10. The dilatation balloon device of claim 1, 2, 3, 4, 5, 6 or 7 wherein helical coil means extend from the proximal region to the distal end of the device.

11. The dilatation balloon device of claim 1, 2, 3, 4, 5, 6 or 7 wherein a helical coil extends over a hollow liquid-tight tube from the proximal region of the device to the distal region of said main tubular body and a fluid impermeable sleeve extends from said distal region of said tubular body to said balloon.

12. The dilatation balloon device of claim 1, 2, 3, 4, 5, 6 or 7 wherein flexible polymeric tube means extend from the proximal region of the device to the proximal portion of said balloon.

13. The dilatation balloon of claim 1, 2, 3, 4, 5, 6 or 7 wherein said main tubular body comprises an exterior heat shrink tube shrunk upon a hollow metal liquid-conducting tube.

14. The dilatation balloon device of claim 1 or 7 wherein said balloon is the product of the process of blowing and drawing a preformed tubular member having a tapered contour in the region corresponding to the transition section of the blown balloon.

15. The dilatation balloon device of claim 14 wherein the preformed tubular member is the product of heating and drawing a defined region of an extruded tube of originally constant diameter and wall thickness.

16. The dilatation balloon device of claim 14 wherein the wall thickness of said tapering transition section is about the same as the wall thickness of the main body of the balloon.

17. The dilatation balloon catheter of claim 14 wherein the wall thickness of said tapering transition section is less than the wall thickness of the main body of the balloon.

18. The dilatation balloon catheter of claim 14 wherein the main body of said balloon has an inflated diameter of 5 mm or larger.

19. The dilatation balloon catheter of claim 14 wherein the resin from which the balloon is formed is polyethylene terephthalate.

20. The dilatation balloon device of claim 14 wherein an elongated sleeve extending proximally from said balloon past said inflation opening is formed integrally with said balloon as a result of drawing said tubular member.

21. The dilatation balloon device of claim 14 wherein said balloon has sleeves of smaller diameter than the original diameter tube from which the sleeves are formed.

* * * * *

UNITED STATES PATENT AND TRADEMARK OFFICE
CERTIFICATE OF CORRECTION

PATENT NO. : 4,906,241

DATED : March 6, 1990

INVENTOR(S) : Richard A. Noddin et al.

It is certified that error appears in the above-identified patent and that said Letters Patent is hereby corrected as shown below:

On the title page, item [54] and column 1, line 2, in the Title:
   Change "DILATION" to --DILATATION--;

In the Abstract:

Line 1, "Dilation" should be --Dilatation--;
   Col. 1, Title, "DILATION" should be --DILATATION--;
   Line 68, "deice" should be --device--;
   Col. 2, line 26, "providinq" should be --providing--;
   Col. 3, line 6, "he" should be --the--;
   Col. 5, line 66, "e" should be --e.--;
   Col. 10, line 7, delete "that extends" before "from" (2nd occurrence).

Signed and Sealed this

Twenty-fifth Day of June, 1991

*Attest:*

HARRY F. MANBECK, JR.

*Attesting Officer*    *Commissioner of Patents and Trademarks*